us 009730667B2

(12) United States Patent
Machida

(10) Patent No.: US 9,730,667 B2
(45) Date of Patent: Aug. 15, 2017

(54) CONTROL APPARATUS AND TOMOGRAPHY APPARATUS

(71) Applicant: CANON KABUSHIKI KAISHA, Tokyo (JP)

(72) Inventor: Yoshihito Machida, Sagamihara (JP)

(73) Assignee: Canon Kabushiki Kaisha, Tokyo (JP)

( * ) Notice: Subject to any disclaimer, the term of this patent is extended or adjusted under 35 U.S.C. 154(b) by 128 days.

(21) Appl. No.: 14/599,343

(22) Filed: Jan. 16, 2015

(65) Prior Publication Data
US 2015/0201898 A1  Jul. 23, 2015

(30) Foreign Application Priority Data

Jan. 20, 2014  (JP) .................................. 2014-008116

(51) Int. Cl.
*A61B 6/03* (2006.01)
*A61B 6/00* (2006.01)
*A61B 6/04* (2006.01)
*G21K 1/10* (2006.01)

(52) U.S. Cl.
CPC ............ *A61B 6/542* (2013.01); *A61B 6/0421* (2013.01); *A61B 6/4035* (2013.01); *A61B 6/4441* (2013.01); *A61B 6/502* (2013.01); *G21K 1/10* (2013.01); *A61B 6/4233* (2013.01)

(58) Field of Classification Search
CPC ......... A61B 6/03; A61B 6/032; A61B 6/0421; A61B 6/4035; A61B 6/4233; A61B 6/4441; A61B 6/502; A61B 6/542; G21K 1/02; G21K 1/04; G21K 1/043; G21K 1/10
See application file for complete search history.

(56) References Cited

U.S. PATENT DOCUMENTS

| 5,506,877 A * | 4/1996 | Niklason ................ A61B 6/502 378/208 |
| 5,627,869 A * | 5/1997 | Andrew ................. A61B 6/502 378/150 |
| 6,307,918 B1 * | 10/2001 | Toth ........................ A61B 6/032 378/156 |
| 9,316,601 B2 * | 4/2016 | Proksa .................... A61B 6/032 |
| 2005/0013411 A1 * | 1/2005 | Yahata ..................... A61B 6/06 378/156 |
| 2010/0177866 A1 * | 7/2010 | Shibuya ................. A61B 6/032 378/20 |
| 2010/0177886 A1 * | 7/2010 | Futa ......................... G06F 7/723 380/28 |

(Continued)

FOREIGN PATENT DOCUMENTS

JP  2005-034173 A  2/2005

*Primary Examiner* — David E Smith
(74) *Attorney, Agent, or Firm* — Canon USA, Inc. I.P. Division

(57) ABSTRACT

A tomography apparatus for readily imaging an object while reducing radiation exposure doses includes a filter that adjusts distribution of a radiation dose transmitted therethrough from a radiation source, a radiation detection unit that detects a radiation dose transmitted through the filter and through an object, a holder that holds the object, an acquisition unit that acquires information about the holder, and a control unit that controls the distribution of the transmitted radiation does according to the information about the holder acquired by the acquisition unit.

13 Claims, 13 Drawing Sheets

(56) References Cited

U.S. PATENT DOCUMENTS

| | | | |
|---|---|---|---|
| 2011/0075799 A1* | 3/2011 | Okada | A61B 6/022 378/41 |
| 2012/0238870 A1* | 9/2012 | Smith | A61B 6/025 600/431 |
| 2013/0281840 A1* | 10/2013 | Vaughan | A61B 6/0414 600/425 |

* cited by examiner

FIG. 7

| HOLDER | (a) | (b) | (c) | (d) | (e) | (f) |
|--------|-----|-----|-----|-----|-----|-----|
| FILTER | (A) | (B) | (C) | (D) | (E) | (F) |

FIG. 11

| DIAMETER OF BREAST INSERTION UNIT (BREAST INSERTION HOLE) | 70 mm | 85 mm | 100 mm | 115 mm | 130 mm | 150 mm |
|---|---|---|---|---|---|---|
| THICKNESS OF PLATE FILTER | 2 mm | 2 mm | 3 mm | 3 mm | 4 mm | 5 mm |
| DISTANCE BETWEEN SLOPE FILTERS | 0 | 2 mm | 5 mm | 8 mm | 11 mm | 15 mm |
| DISTANCE BETWEEN COLLIMATORS | 15 mm | 17 mm | 20 mm | 23 mm | 26 mm | 30 mm |

CONTROL APPARATUS AND TOMOGRAPHY APPARATUS

BACKGROUND

Field

Aspects of the present invention generally relate to an apparatus for performing tomography on an object using radiation, and in particular, to an apparatus for performing breast tomography.

Description of the Related Art

In tomography, portions put on an image pickup area often have different cross-sectional shapes according to objects. In particular, in a tomography apparatus for breast inspection, when a dose of radiation to be delivered to photograph a portion having a large cross-sectional shape is increased to uniform the dose of radiation transmitted through the object regardless of the shape of the object, a portion having a small cross-sectional shape is exposed to excessive radiation. Further radiation has a difference in radiation quality due to beam hardening effect according to a transmission length of the object, and the difference in radiation quality causes deterioration in quality of a reconstructed image.

For reduction in dose of radiation to which the object is exposed and uniform dose distribution or radiation quality, as described above, a filter called wedge filter is known which controls dose distribution or radiation quality. The wedge filter is a filter provided between a radiation generator and the object. As the wedge filter, a filter called a bowtie filter is known. The bowtie filter has a shape having a thickness small at the center corresponding to a major part of the object and large at the peripheral part corresponding to a minor part of the object. Japanese Patent Application Laid-Open No. 2005-034173 discloses a technique for obtaining an X-ray intensity distribution desirably adjusted using an X-ray distribution adjusting filter provided with a bellows-shaped movable portion.

However, in Japanese Patent Application Laid-Open No. 2005-034173, the filter is complicatedly adjusted to be matched with the shape of the object. Accordingly, the filter is less matched with the shape of the object, and an unnecessary dose of radiation to which the object is exposed, is insufficiently reduced.

SUMMARY OF THE INVENTION

According to an aspect of the present invention, a tomography apparatus is provided for readily imaging an object using a suitable filter to reduce exposure dose.

A tomography apparatus according to an exemplary embodiment includes a filter configured to adjust distribution of a radiation dose transmitted therethrough from a radiation source, a radiation detection unit configured to detect radiation transmitted through the filter and through an object, a holder configured to hold the object, an acquisition unit configured to acquire information about the holder, and a control unit configured to control the distribution of a transmitted radiation dose according to the information about the holder acquired by the acquisition unit.

Further features of the present disclosure will become apparent from the following description of exemplary embodiments with reference to the attached drawings.

BRIEF DESCRIPTION OF THE DRAWINGS

FIG. 7 is a table illustrating exemplary combinations between the breast insertion units and filters according to the first exemplary embodiment.

FIG. 11 is a table illustrating exemplary combinations of thicknesses of plate filter units, distances between slope filters, and distances between collimators of a collimator unit, for respective sizes of breast insertion units.

DESCRIPTION OF THE EMBODIMENTS

Exemplary embodiments will be described below with appropriate reference to the drawings. Here, breast tomography will be described.

First Exemplary Embodiment

Using FIGS. 1 to 8, a first exemplary embodiment will be described in detail.

Figure 1:
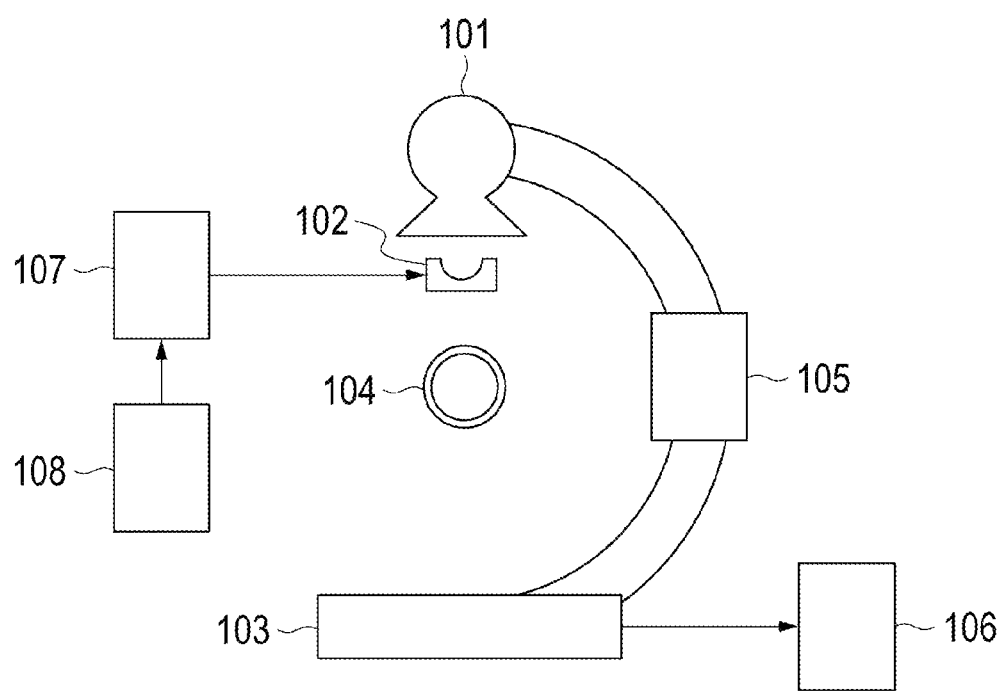
FIG. 1 is a block diagram illustrating a tomography apparatus according to a first exemplary embodiment.

First, a functional configuration of a tomography apparatus 100 will be descried according to FIG. 1. The tomography apparatus of FIG. 1 includes a radiation source 101, filters 102, a radiation detector 103, a holder 104, an apparatus rotation unit 105, an image reconstruction unit 106, a control unit 107, and an acquisition unit 108.

The radiation source 101 emits radiation to an object, and the filter 102 adjusts a distribution of radiation dose transmitted therethrough from a radiation source 101. The radiation detector 103 detects, through the filter 102, the radiation transmitted through the object, and generates image data. The acquisition unit 108 is configured to acquire object information. The control unit 107 controls the distribution of transmitted dose according to the object information having been acquired by the acquisition unit 108. It is assumed that the object information acquired by the acquisition unit 108 includes at least one of the transmissivity of the object, the shape of the object, the shape or material of the holder 104, and the shape of the object defined by a shape of the holder 104 as mentioned below. The tomography apparatus 100 previously includes a plurality of the filters 102, and the control unit 107 selects one filter 102 from among the filters 102, when controlling the distribution of transmitted dose. Further, in order to control the transmission dose, the control unit 107 is allowed to determine a combination of a plurality of materials each absorbing radiation, and changes a shape of the filter 102. According to this configuration, a suitable filter is selected for the object to reduce a dose of radiation to which the object is exposed. Further, the control unit 107 controls the distribution of transmitted dose to control the distribution of transmitted dose for uniform distribution of radiation detected by the radiation detector 103.

The radiation detector 103 is allowed to use, for example, a flat panel detector (FPD) for converting the distribution of transmitted dose to digital signals and obtaining the image data.

Further, the holder 104 is configured to hold the object in a predetermined shape. In the present exemplary embodiment, the object as a breast will be described below. The holder 104 holds the breast in the predetermined shape.

The apparatus rotation unit 105 movably rotates the radiation source 101, the filters 102, and the radiation detector 103 along the outer periphery of the holder 104. The image reconstruction unit 106 performs reconstruction processing using a plurality of pieces of image data having been obtained from the radiation detector 103, and generates tomographic image.

The acquisition unit 108 has the object information having been acquired from an external input or information having been obtained in a system, and can transmit the information to the control unit 107. The external input is performed by an input/output device (not illustrated) such as a mouse, a keyboard, or a touch panel, and the acquisition unit 108 can receive and acquire the object information having been input. The acquisition unit 108 may be integrated with the input/output devices. The acquisition unit 108 stores the object information in a storage medium such as a hard disk. Here, each component illustrated in FIG. 1 includes dedicated hardware.

It is noted that, in the present exemplary embodiment, the breast corresponds to the object and the radiation detector 103 corresponds to radiation detection unit.

Figure 2:
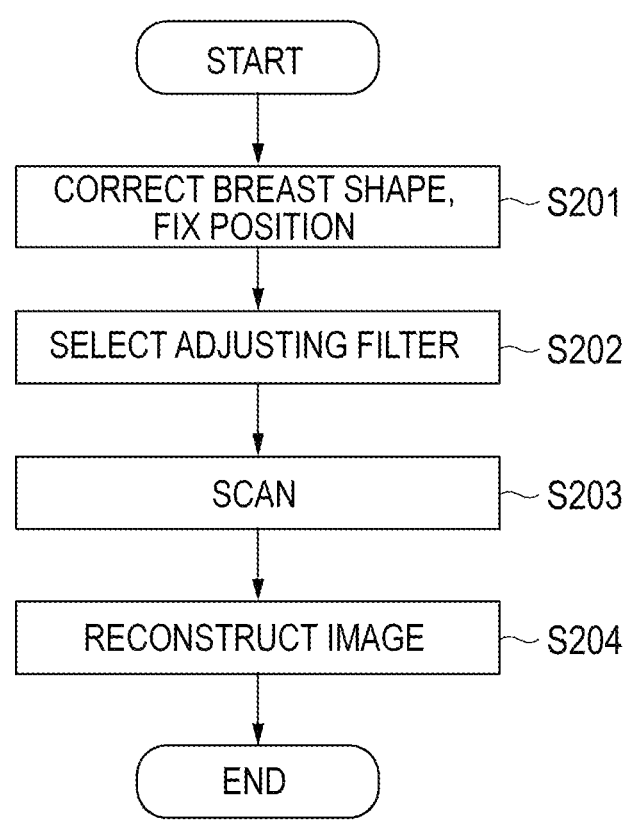
FIG. 2 is a flowchart illustrating operation of the tomography apparatus according to the first exemplary embodiment.

Next, according to FIG. 2, operation of the tomography apparatus 100 of FIG. 1 will be descried. In step S201, the holder 104 corrects the breast to have a circular cross-sectional shape. Further, the holder 104 is fixed to align an axis perpendicular to a center point of a cross-section having a breast insertion hole 304 described below, i.e., a center point of a circle of the breast insertion hole 304, with a rotation axis of the rotation unit 105 of the tomography apparatus 100. Then, the breast is sucked and held by a breast suction unit 302 so that the breast is not moved during tomography. It is noted that a diameter of a circle corrected by the holder 104 is determined according to a breast size of the object. A configuration of the holder 104 and a process of holding the breast in the holder 104 will be described later.

In step S202, the control unit 107 selects one filter 102 according to the object information acquired by the acquisition unit 108 to adjust the distribution of transmitted dose. A process of changing the filters 102 in the control unit 107 will be described later in detail.

In step S203, the apparatus rotation unit 105 rotates the radiation source 101, the filters 102, and the radiation detector 103 about the holder 104, changes an radiation angle to deliver radiation from the radiation source 101, and collects image data. Hereinafter, this series of operation is called scanning operation. During the scanning operation, the cross-section of the breast is defined to the circular shape by the holder 104, and the filters 102 are changed by the control unit 107 so that the distribution of transmitted dose is changed according to the cross-sectional shape of the breast. For this reason, even if the radiation source 101 irradiates the breast at any radiation angle, the distribution of transmitted dose detected by the radiation detector 103 is uniformed, after the dose is transmitted through the breast. Therefore, the tomography apparatus 100 can perform tomography at each radiation angle without controlling the position or the shape of the filter 102. As a result, generation of the dose of radiation to which the object is exposed is reduced, and generation of the beam hardening effect is inhibited.

In step S204, the image reconstruction unit 106 reconstructs image data obtained by the scanning operation, and obtains a tomographic image of the object. The reconstruction processing preferably uses filtered back projection, iterative reconstruction, or the like.

As described above, generation of a tomographic image by the tomography apparatus 100 is completed through the operation of steps S201 to S204.

Next, defining the shape of the object and holding the object, in the holder 104, will be described in detail using FIGS. 3 and 4.

Figure 3:
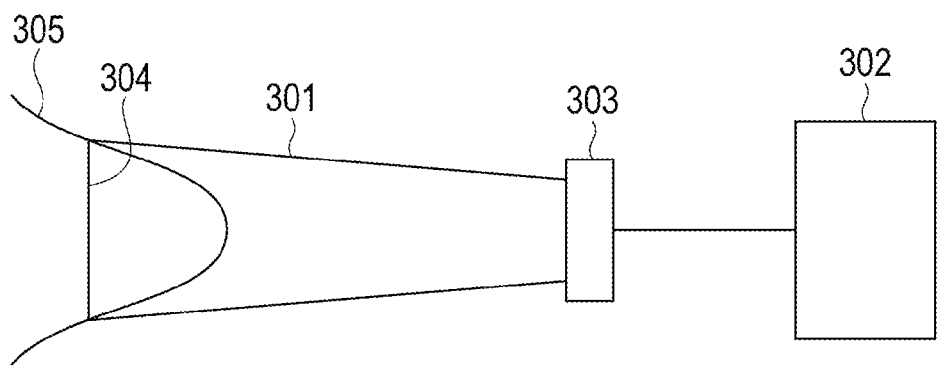
FIG. 3 is an exemplary diagram illustrating a holder and a suction unit according to the first exemplary embodiment.

FIG. 3 is an exemplary schematic view illustrating the holder 104. The holder 104 includes the breast insertion hole 304, a breast insertion unit 301, and a holder side fixing unit 303. The breast insertion hole 304 receives the breast inserted. The breast insertion unit 301 covers the breast. The holder side fixing unit 303 fixes the holder 104 to the tomography apparatus 100. When the breast is held, the breast suction unit 302 is connected to the holder 104, sucks air in the breast insertion unit 301, sucks the breast toward the inner peripheral surface of the breast insertion unit 301, defines the shape of the breast, and holds the breast.

Figure 4:
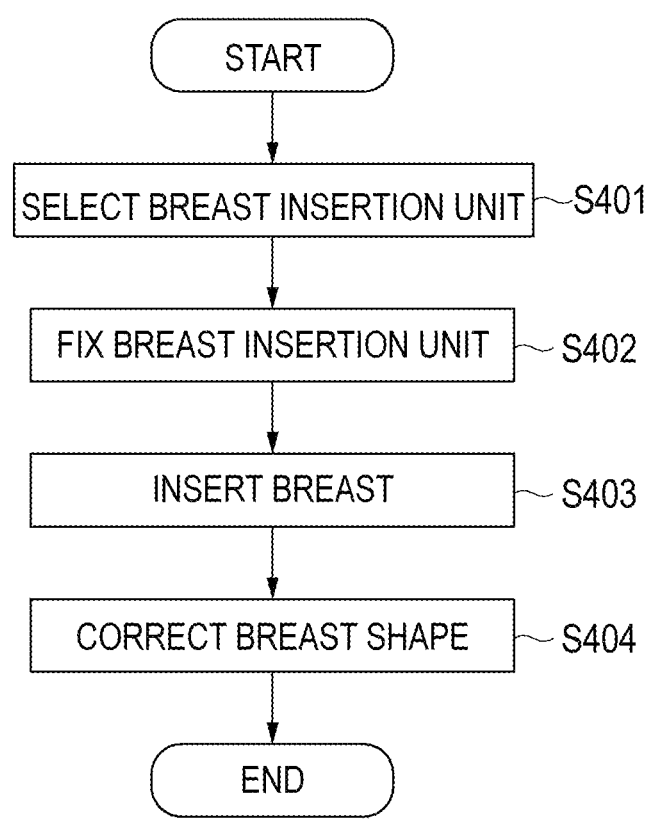
FIG. 4 is a flowchart illustrating operation of the holder.

FIG. 4 is a flowchart illustrating operation of defining the shape of the breast and holding the breast, using the holder 104. In step S401, an operator (not illustrated) selects one from the breast insertion units 301 according to the shape or size of the breast.

In step S402, a fixing unit (not illustrated) in the tomography apparatus 100 fixes the breast insertion unit so that the center of the breast insertion unit 301 is aligned with the rotation axis of the tomography apparatus 100. A fixing process may preferably include fixing the breast insertion unit using the holder side fixing unit 303 on the outside of the breast insertion unit 301 and an electromagnet stuck to the fixing unit, fixing the breast insertion unit by sucking the holder 104 itself by the fixing unit, or fixing the breast insertion unit by providing a hook or the like on the holder side fixing unit 303. With the above-mentioned configuration, the center axis of the breast can be fixed to be aligned with the rotation axis of the tomography apparatus 100.

In step S403, the breast as the object is inserted into the breast insertion unit 301.

In step S404, the breast suction unit 302 sucks and holds the breast having inserted into the breast insertion unit 301. With the above-mentioned configuration, the breast is brought into close contact with the inner peripheral part of the breast insertion unit 301 without a gap, and the breast can be corrected to have a shape following the breast insertion unit 301. In the present exemplary embodiment, the breast is corrected to have a circular cross-sectional shape following the breast insertion unit 301, so that the filter 102 can have a fixed shape regardless of the radiation angle of the radiation source 101.

Operation of correcting and holding the breast by the holder 104 is completed through the operation of steps S401 to S404, and the holder 104 allows for alignment of the center axis of the breast corrected to have a circular shape, with the rotation axis of the tomography apparatus 100. It is noted that the order of step S402 and steps S403 and S404 may be reversed to insert the breast into the breast insertion unit 301, and suck and fix the inserted breast.

Next, a radiation distribution adjustment process in the control unit 107 will be described in detail using FIGS. 5 to 7.

Figure 5:
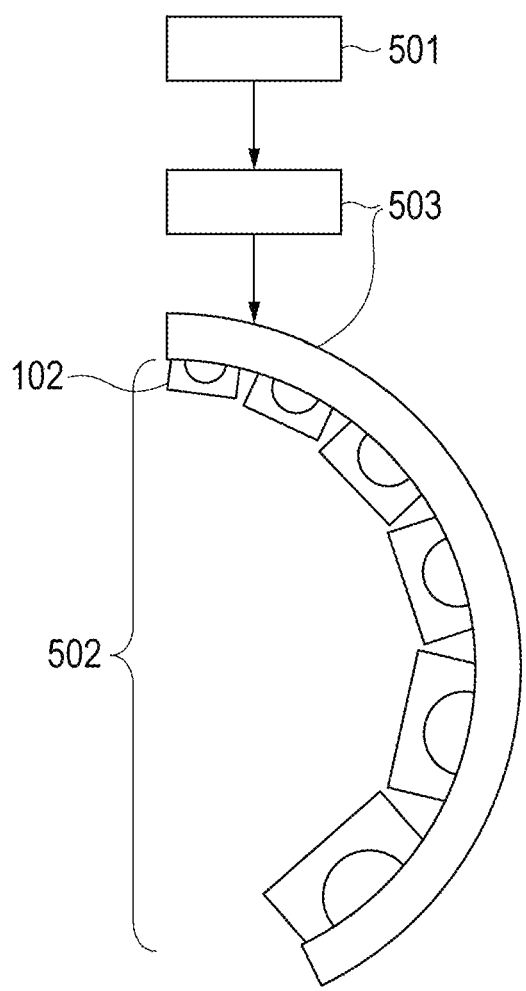
FIG. 5 is an exemplary diagram illustrating a control unit 107 according to the first exemplary embodiment.

FIG. 5 is an exemplary diagram illustrating the control unit 107. The control unit 107 includes a filter shape selection unit 501, a filter installation unit 503, and a filter unit 502 having a plurality of filters.

The filter shape selection unit 501 selects one optimal filter from the filter unit 502 according to the object information having been acquired from the acquisition unit 108, and outputs the information to the filter installation unit 503. The filter shape selection unit 501 holds information about combinations between the object information and the filters, in a storage medium or the like.

Figure 6:
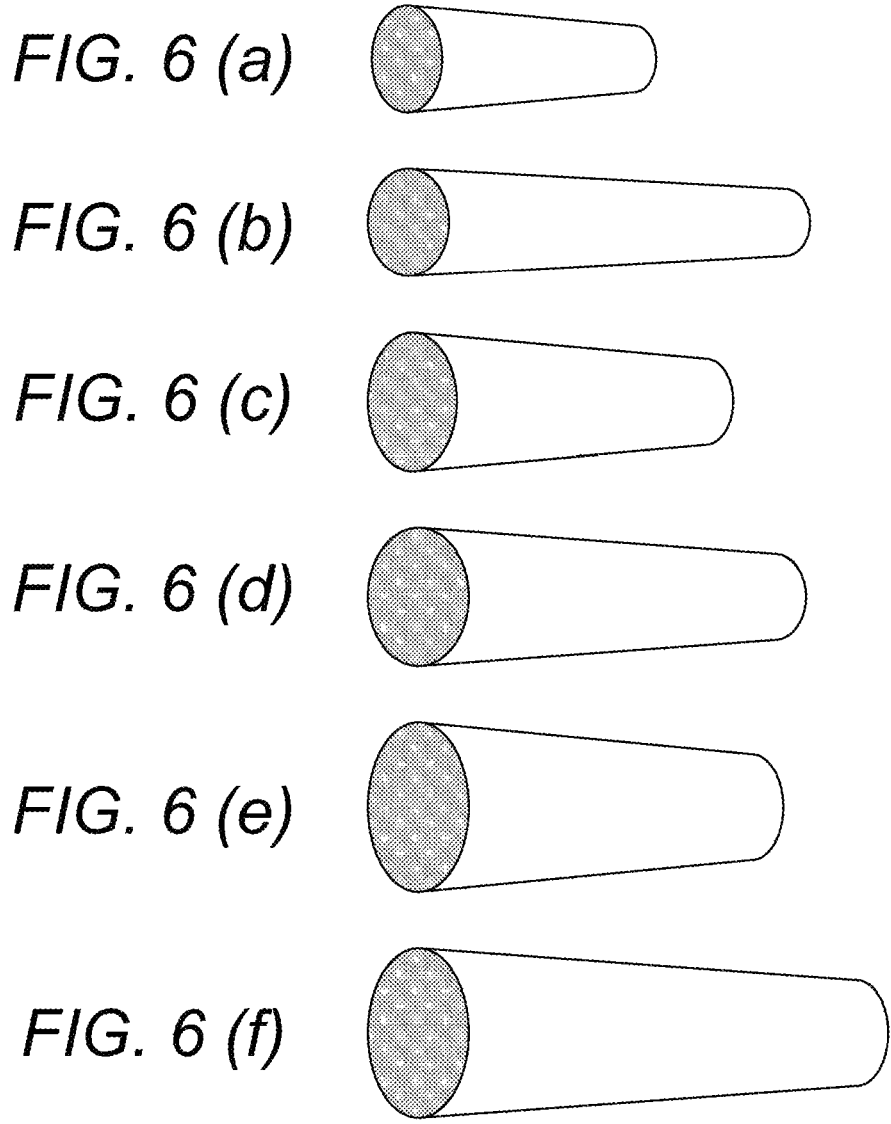
FIGS. 6(a)-6(f) are an exemplary diagram illustrating breast insertion units according to the first exemplary embodiment.

FIGS. 6(*a*)-6(*f*) are an exemplary diagram illustrating the breast insertion units 301 by size. The filter shape selection unit 501 can select one from shapes (a) to (f) according to the object information about the size or length of the breast.

Figure 7:
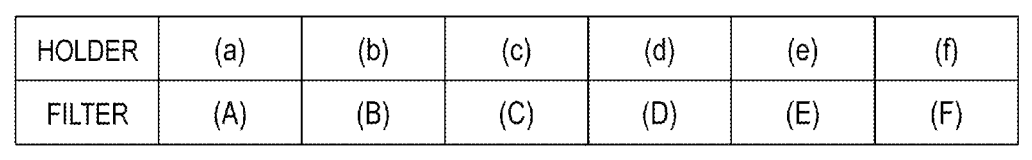

FIG. 7 is a table illustrating exemplary combinations of the breast insertion units 301 and corresponding filters selected respectively from the filter unit 502 according to the breast insertion units 301. According to the shape of the breast insertion unit 301, the distribution of transmitted dose is different in desired adjustment range, and the filter 102 is also different in suitable shape. Therefore, the filter shape selection unit 501 is configured to select one from shapes (A) to (F) according to the shape of the breast insertion unit 301. The shape of the filter will be described later in detail. The filter installation unit 503 has a plurality of filters 102 installed to be selected by the filter shape selection unit 501. In FIG. 5, the filters 102 having different shapes are circumferentially arranged between the breast and a trajectory in which the radiation source 101 is rotationally moved around the breast. The filter installation unit 503 has a driving mechanism to rotate the filters 102 circumferentially arranged, about a rotational shaft. Accordingly, the filters 102 used for tomography can be changed. The filters are installed so that a center position of the filter 102 is located on a straight line connecting a focal position of the radiation source 101, a rotation axis thereof, and the radiation detector 103.

It is noted that the filter changing process in the filter installation unit 503 may not employ the above-mentioned process, but may employ, for example, a process of taking out the filter 102 from the filter installation unit 503 by the operator for replacement. Further, the filter installation unit 503 may not have a shape illustrated in FIG. 5, but may be configured so that the filters are installed in a direction perpendicular to a straight line connecting the focal position of the radiation source 101 and the radiation detector 103 to change the shape of the filter.

Figure 8A:
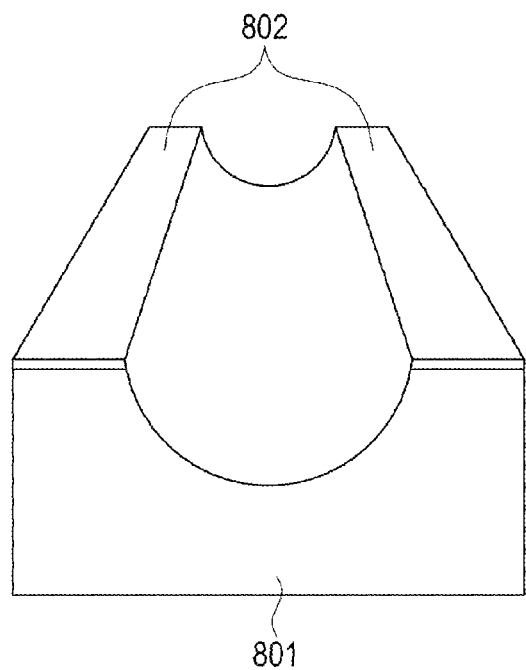
FIGS. 8A, 8B, and 8C are schematic views illustrating a filter according to the first exemplary embodiment.
Figure 8B:
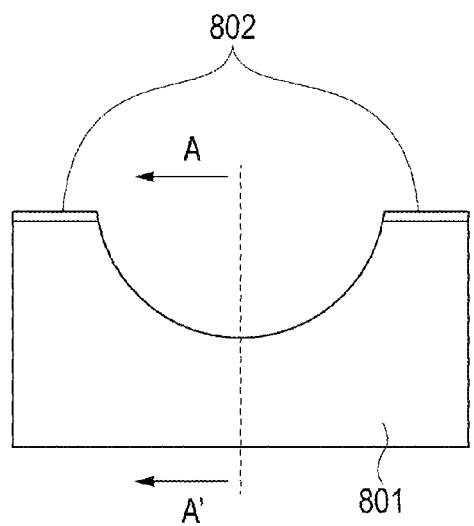
Figure 8C:
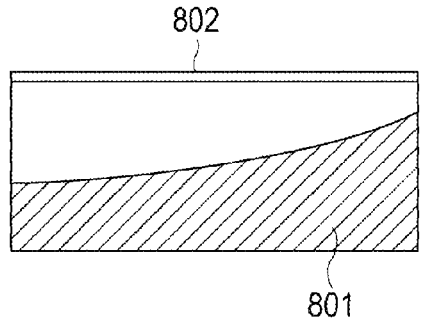

The filter of the present exemplary embodiment will be described in detail using FIG. 8. FIG. 8A is a perspective view of the filter, FIG. 8B is a front view of the filter, and FIG. 8C is a cross-sectional view of the filter taken along the line A-A' of FIG. 8B. In FIGS. 8A to 8C, 801 denotes a wedge filter unit 801 through which radiation emitted from the radiation source 101 is transmitted to photograph the breast in the breast insertion unit 301.

802 denotes a collimator unit configured to reduce an intensity of radiation delivered to a portion other than the breast, to a value equal to or less than a predetermined value. A shape of the wedge filter unit 801 is determined according to the shape of the breast insertion unit 301, a material thereof, or radiation transmittance of the breast. The breast insertion unit 301 has a shape in which a diameter tapers toward a nipple side, so that the wedge filter unit 801 also has a thickness increasing toward the nipple side from the breast insertion hole 304 according to the shape of the breast insertion unit. The configuration indicates that the breast inserted into the breast insertion unit 301 tapers toward the nipple side, when sucked and defined in shape. Since the breast tapers toward the nipple side, correction is facilitated.

The thickness of the wedge filter unit 801 may only be configured to uniform the transmission dose being radiation transmitted through the wedge filter unit 801, the breast insertion unit 301, and the breast. A thickness of the wedge filter unit 801 is preferably determined so that the transmission dose is uniformed at each radiation angle based on the transmission dose on a side nearest to a chest wall, from the radiation source 101 to the radiation detector 103 through the central axis of the breast. Specifically, mammary tissue and adipose tissue occupy a major part of the breast, so that the attenuation rate of radiation is substantially constant in the breast, and the transmission dose can be readily uniformed over the whole of the breast by a process of determining the shape of the wedge filter unit 801 according to the present exemplary embodiment. Further, when the transmission dose is determined as a reference by the radiation detector 103, a plate filter (not illustrated) configured to inhibit exposure to excessive radiation is preferably inserted. In this configuration, a minimum number of plate filters and wedge filter units 801 may be integrated. Further, a thickness of the plate filter is also preferably changed according to the object information.

Here, description will be made of reduction in artifacts generated in the tomographic image. The artifacts are caused by change in radiation quality, called beam hardening effect, upon transmission through the object. In this case, the shape of the wedge filter unit 801 may only be formed to have a uniform change in quality of radiation transmitted through the wedge filter unit 801, the breast insertion unit 301, and the breast uniform, as far as possible. The shape formed as described above can improve accuracy of CT values at each radiation angle and reduce the artifacts.

Further, when adjustment of both of the distribution of transmitted dose and radiation quality distribution is desired, the shape of the filter may be determined by combining the distribution of transmitted dose and the radiation quality distribution.

When the wedge filter unit 801 has a material having an attenuation rate equivalent to that of the breast, the thickness of the wedge filter unit 801 is readily determined. Further for reduction in size of tomography apparatus 100, for example, a metal having a high attenuation rate of radiation may be employed. At that time, a plurality of metals, such as aluminum and copper, may be combined for use as a material of the wedge filter unit 801.

Next, 802 denotes collimator unit configured to reduce the intensity of radiation delivered to the portion other than the breast in the breast insertion unit 301, to the value equal to or less than the predetermined value. Here, the predetermined value is desirably configured to define the intensity of radiation, to an extent not exceeding a permissible radiation dose of the radiation detector 103, and preventing the effect of scattering radiation caused by unnecessary radiation.

In FIG. 8, the collimator unit 802 is disposed at a flat portion of the wedge filter unit 801. The shape of the breast is defined by the holder 104, and the breast is fixed at the rotation axis of the tomography apparatus 100 by the fixing unit, the portion other than the breast is previously understood before photographing. Therefore, a size of the collimator unit 802 can be determined based on a spread of radiation delivered from the radiation source 101 and a size of the breast insertion unit 301.

The collimator unit 802 preferably includes a material having a high radiation absorption rate, such as tungsten or lead. As described above, the size of the collimator unit 802 is determined according to the shape of the breast insertion unit 301. Therefore, by providing the collimator unit 802, unnecessary radiation delivered to the portion other than the breast is prevented without a complicated driving mechanism or control mechanism, such as a movable collimator. In this way, unnecessary radiation is prevented, the scattering radiation is prevented, and image quality is improved. Further, radiation out of the allowable range is also not delivered to the radiation detector 103, so that saturation of pixel values can be prevented.

In the present exemplary embodiment, the breast insertion unit 301 has shapes as illustrated in FIGS. 6(a)-6(f), but the breast insertion unit 301 may have a substantially semi-spherical shape. In this structure, when the collimator unit is made to fit the semi-spherical shape, unnecessary radiation is also prevented on the nipple side. Further, when the breast insertion unit 301 has shapes as illustrated in FIGS. 6(a)-6(f), unnecessary radiation is prevented on the nipple side by providing another movable collimator only on the nipple side. As described above, exposure dose can be reduced by making the shape of the filter to fit the shape of the holder.

It is noted that the number of filters to be selected may not be the same as that of breast insertion units 301 to be selected. For example, the number of filters selected, structurally restricted to three, will be described.

In FIGS. 6(a)-6(f), for the shapes of (a) to (b) of the breast insertion unit 301, the shape (A) of the wedge filter unit 801 is preferably used, for the shapes of (c) to (d) of the breast insertion unit 301, the shape (C) of the wedge filter unit is preferably used, and for the shapes of (e) to (f) of the breast insertion unit 301, the shape (E) of the wedge filter unit is preferably used. In this way, when the number of filters is restricted, insufficient radiation dose can be prevented by selecting the filter of a smaller size. Alternatively, when the filter of a larger size is selected, the increase of the exposure dose can be prevented.

In addition, when the number of selectable filters is larger than the number of breast insertion units 301, the filters are allowed to be changed between them according to the difference in radiation quality, such as set tube voltages between the breast insertion units 301 of the same shape, percentage of mammary gland and adipose of the object, a material of a cup, or the object information. In the present exemplary embodiment, description has been made of changing the shape of the filter 102 according to the object information. However, alternatively, the shape of the filter may be changed according to information about another object to be photographed, such as a material of the holder 104, a cross-sectional area of the breast or a length thereof from the chest wall portion, a distance between a focal point of the radiation source 101 and the radiation detector 103, or a distance between the focal point of the radiation source 101 and the breast.

As described above, reduction in exposure dose, improvement in image quality, or improvement in CT value accuracy is achieved by adjusting the distribution of transmitted dose according to the object information.

Second Exemplary Embodiment

In the present exemplary embodiment, a configuration and basic operation of the tomography apparatus, similar to those having been described in the first exemplary embodiment, will be omitted, and only a filter changing process different from the first exemplary embodiment will be described. In the present exemplary embodiment, a control unit 1104 determines a combination of a plurality of materials absorbing radiation, and changes a shape of the filter in order to control transmission dose. A description will be made below using FIGS. 9 to 13.

Figure 9:
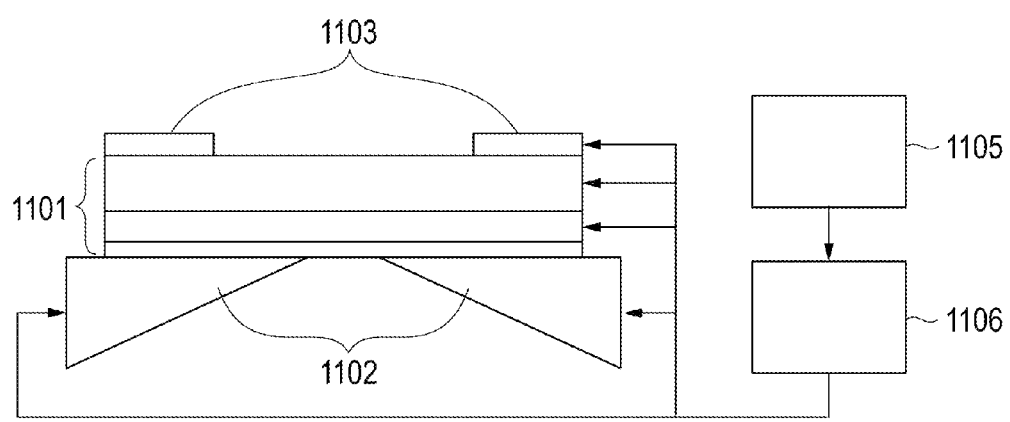
FIG. 9 is an exemplary diagram illustrating a filter unit according to a second exemplary embodiment.

FIG. 9 is an exemplary diagram illustrating a filter unit 1100. The filter unit 1100 includes a plate filter unit 1101, a slope filter unit 1102, and a collimator unit 1103.

The control unit 1104 can change a combination of the filter units or a combination of thicknesses or disposition in each filter unit, according to object information having been acquired by an acquisition unit 108. The control unit 1104 includes a filter shape selection unit 1105 and a filter installation unit 1106, similarly to the first exemplary embodiment. The filter shape selection unit 1105 selects an optimal filter shape according to the object information having been acquired from the acquisition unit 108, and outputs the information to the filter installation unit 1106. In the filter installation unit 1106, filter materials of the filter unit 1100 are disposed. The filter installation unit 1106 has a driving mechanism. The filter installation unit 1106 drives the filter materials to have the filter shape having been selected by the filter shape selection unit 1105. Further, filter installation unit 1106 installs a filter so that the center position of the filter unit 1100 is positioned on a straight line connecting a focal position of a radiation source 101, a rotation axis thereof, and a radiation detector 103.

The plate filter unit 1101 removes low energy radiation not transmitted through an object, and reduces unnecessary exposure dose according to the object information. The plate filter unit 1101 includes one or more plate-shaped material sheets absorbing radiation (plate filter material). The control unit 1104 determines a shape of the plate filter unit 1101 according to the object information. A plurality of plate filter materials are appropriately moved and combined to control the thickness of the plate filter unit 1101.

The slope filter unit 1102 includes a combination of two slope filters having a high radiation absorption rate, and having a slope or an arc. The two slope filters are disposed, at a predetermined interval, symmetrically with respect to a straight line connecting the focal position of the radiation source 101 and the radiation detector 103. The control unit 1104 increases or reduces the predetermined interval to change the thickness of the filter according to the object information.

The collimator unit 1103 is disposed on the top of the plate filter unit 1101, and includes a material absorbing radiation. The collimator unit 1103 reduces the intensity of radiation delivered to a portion other than the object (a breast in a breast insertion unit 301), to a value equal to or less than a predetermined value. Here, a process of determining the predetermined value is assumed to be the same as the process having been described in the first exemplary embodiment. The unnecessary radiation is prevented by the collimator unit 1103, and thus scattering radiation is reduced, and image quality is improved. Further, radiation out of an allowable range is also not delivered to the radiation detector 103, so that saturation of pixel values caused by a radiation dose exceeding a permissible radiation dose can be prevented. Still further, when a movable collimator is also provided on the nipple side, scattering radiation from the nipple side is reduced, and the saturation can be prevented.

In the present exemplary embodiment, the plate filter unit 1101 corresponds to the plate filter, the slope filter unit 1102 corresponds to a slope filter, and the collimator unit 1103 corresponds to the collimator, respectively, according to an embodiment.

Figure 10:
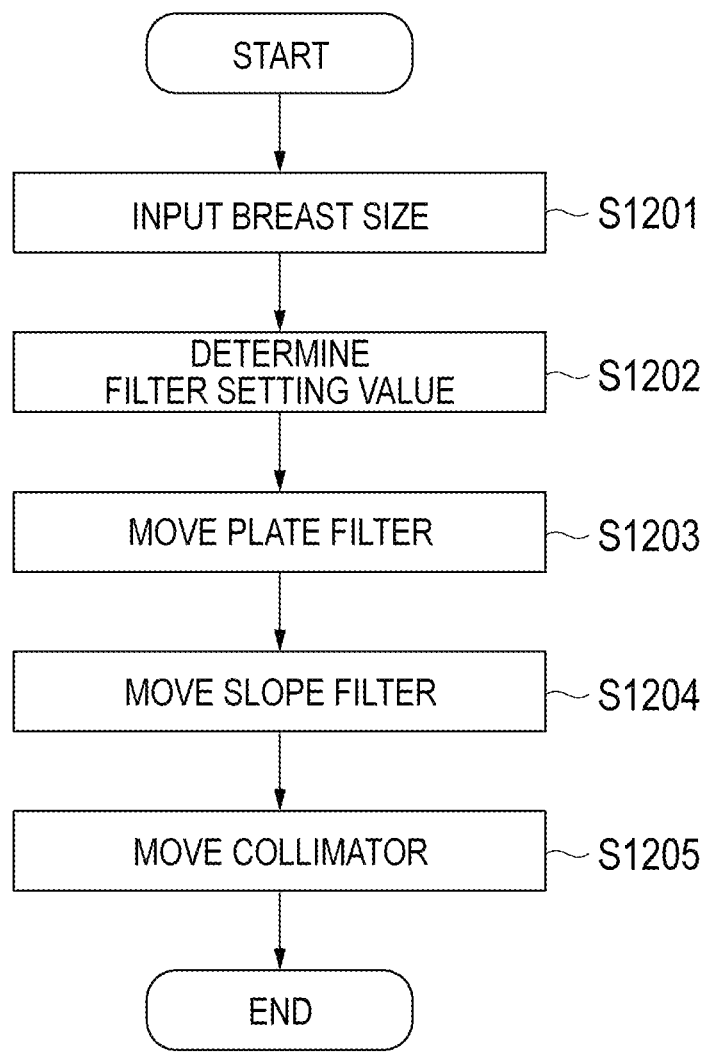
FIG. 10 is a flowchart illustrating a flow of a filter changing process according to the second exemplary embodiment.

Next, a flow of the filter changing process will be described using FIG. 10.

First, an operator inputs a size of the breast insertion unit 301 to the control unit 1104 (S1201).

Next, the control unit 1104 changes the shape of the filter according to the size of the breast insertion unit 301, based on a filter setting value including a thickness of the plate filter unit 1101, a position of the slope filter unit 1102, and a position of the collimator unit 1103 (S1202).

FIG. 11 is a table illustrating exemplary combinations of thicknesses of the plate filter unit 1101 for each size of the breast insertion unit 301, a distance between the slope filter unit 1102, and a distance between collimators of the collimator unit 1103. In FIG. 11, as the diameter of the breast is increased, transmission of radiation is made more difficult, so that a dose of low energy radiation to be absorbed is increased, and the thickness of the plate filter unit 1101 is increased to harden the radiation quality. The control unit 1104 increases the predetermined interval between the two filter materials of the slope filter unit 1102, as the diameter of the breast is increased, in order to fit the shape of the slope filter unit 1102 to the holder 104. The control unit 1104 changes the position of the collimator unit 1103 to a position at which radiation is not delivered to the portion other than the breast, in association with the position of the slope filter unit 1102.

Next, the plate filter materials are moved to change the thickness of the plate filter unit 1101 (S1203). In FIG. 9, the tomography apparatus 100 has the plate filters including the plate filter materials having thicknesses of 1 mm, 2 mm, and 4 mm respectively, in the filter installation unit 1106. The control unit 1104 combines the plate filter materials to change the plate filter unit to have a thickness of a plurality of materials, from 1 mm to 7 mm in 1 mm increments.

Next, the distance between the slope filters of the slope filter unit 1102 is moved by the control unit 1104 (S1204). A process of determining a tilt angle of the slope filter itself includes determining a reference breast size to have a tilt angle according to the breast size. The control unit 1104 controls the distance between the two slope filters to a predetermined distance, according to a dimensional relationship with the reference breast size, and the slope filter unit can correspond to various sizes.

Figure 12A:
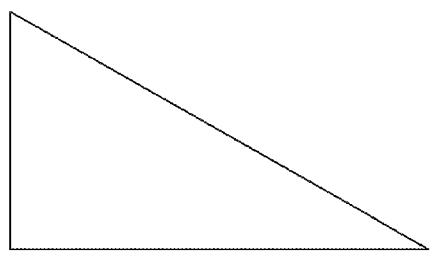
FIGS. 12A and 12B are exemplary diagrams illustrating slope filters according to the second exemplary embodiment.
Figure 12B:
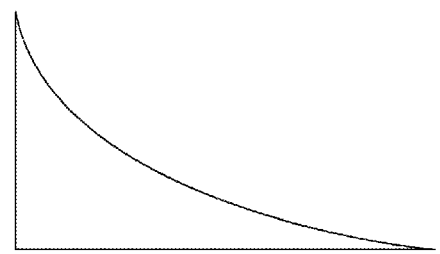

Examples of the slope filters is illustrated in FIGS. 12A and 12B. FIG. 12A is a diagram illustrating the slope filter having a linear slope. FIG. 12B is a diagram illustrating the slope filter having an arcuate slope. Each of the slope filters have a shape ranging from the breast insertion hole 304 to the nipple side, and increasing toward the nipple, according to the shape of the holder 104, similarly to the first exemplary embodiment.

Next, the control unit 1104 moves the collimator unit 1103 (S1205). The control unit 1104 may only move the collimator unit 1103 to a position at which radiation is not delivered to a portion outside the breast insertion unit 301. The collimator unit 1103 prevents unnecessary radiation, so that the scattering radiation is reduced, and the image quality is improved. Further, radiation out of the allowable range is also not delivered to the radiation detector 103, so that the saturation of pixel values can be prevented. Still further, when a movable collimator is also provided on the nipple side, the scattering radiation from the nipple side is reduced, and the saturation of pixel values can be prevented.

It is noted that, in the present exemplary embodiment, the plate filter unit 1101 desirably includes a metal having a low radiation absorption rate, such as aluminum, and the slope filter unit 1102 desirably includes a metal having a high radiation absorption rate, such as copper. When the plate filter unit 1101 and the slope filter unit 1102 include the metal having a low radiation absorption rate, an increase in thickness of the filter unit 1100, as a whole, may cause a problem of disposition of the filter. When the slope filter unit 1102 relatively tending to have a large thickness includes the metal having a high radiation absorption rate, the filter unit 1100 can be appropriately disposed.

In the present exemplary embodiment, the control unit 1104 is configured to move both of the plate filter unit 1101, and the slope filter unit 1102. However, the control unit 1104 may fix the plate filter unit 1101, and moves only the slope filter unit 1102. Further, the process may be configured to change only the plate filter unit 1101, and not to change the slope filter unit 1102. Such a configuration simplifies the configuration of the apparatus.

Figure 13:
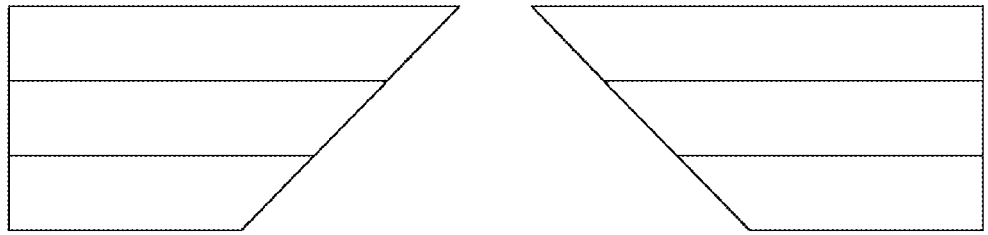
FIG. 13 is an exemplary diagram illustrating the slope filter according to the second exemplary embodiment.

Further, the slope filter unit 1102 may be configured to form a slope surface having a predetermined angle by combining a plurality of materials each having a slope surface. An example of the slope filter unit 1102 having a plurality of layered material sheets each having a slope surface is illustrated in FIG. 13. In this configuration, according to the object information, the control unit 1104 shifts and disposes the plurality of materials each having a slope surface, and thus the slope of the slope filter unit 1102 can control the transmission dose.

Further, the thickness of the slope filter unit 1102 may be fully increased at an end to omit the collimator unit 1103. Such a configuration simplifies a configuration of the control unit 1104.

Other Embodiments

Additional embodiment(s) can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that these exemplary embodiments are not seen to be limiting. The scope of the following claims is to be accorded the broadest interpretation so as to encompass all such modifications and equivalent structures and functions.

This application claims the benefit of Japanese Patent Application No. 2014-008116, filed Jan. 20, 2014, which is hereby incorporated by reference herein in its entirety.

What is claimed is:

1. A tomography apparatus comprising:
a filter configured to adjust distribution of a radiation dose;
a radiation detection unit configured to detect a radiation dose transmitted through the filter and through an object,
wherein the filter comprises:
a plate filter including plate-shaped materials; and
a slope filter having two materials each having a slope surface, and disposed, at a predetermined interval, symmetrically with respect to a straight line connecting a focal point of a radiation source and the radiation detection unit, and
wherein the shape of the filter is obtained by combining the plate filter and the slope filter.

2. A tomography apparatus according to claim 1, further comprising:
an acquisition unit configured to acquire information about the object; and
a control unit configured to control the distribution of the transmitted radiation dose according to the information about the object acquired by the acquisition unit.

3. The tomography apparatus according to claim 2, wherein the control unit controls the distribution of the transmitted radiation dose by selecting one filter from a plurality of filters.

4. The tomography apparatus according to claim 2, further comprising:
a holder configured to hold the object,
wherein,
the acquisition unit acquires information about the holder and
the control unit controls the distribution of the transmitted radiation dose according to the information about the holder acquired by the acquisition unit.

5. The tomography apparatus according to claim 4, wherein the control unit controls the distribution of the transmitted radiation dose by determining a combination of a plurality of materials absorbing radiation according to the information about the holder and changing the shape of the filter.

6. The tomography apparatus according to claim 4, wherein the holder holds a breast as the object in a predetermined shape,
the acquisition unit acquires information about a shape of the holder, and
the control unit controls the distribution of the transmitted radiation dose according to the information about the shape of the holder.

7. The tomography apparatus according to claim 6, wherein, the holder comprises:
an insertion hole configured to receive the breast;
an insertion unit configured to cover the breast; and
a suction unit connected to the holder, the suction unit configured to suck air in the insertion unit to hold the breast on an inner peripheral surface of the insertion unit.

8. The tomography apparatus according to claim 7, further comprising:
a rotation unit configured to rotationally move the radiation source, the filter, and the radiation detection unit along an outer periphery of the holder; and
a fixing unit configured to fix the holder,
wherein the fixing unit fixes the holder to align an axis perpendicular to a center point of a plane having the insertion hole of the holder with a rotation axis of the rotational movement.

9. The tomography apparatus according to claim 7, wherein the breast sucked by the suction unit has a circular cross-sectional shape.

10. The tomography apparatus according to claim 2, wherein the control unit controls a thickness of the plate filter by combining a plurality of the plate-shaped materials according to the information about the holder.

11. The tomography apparatus according to claim 2, wherein the control unit controls the predetermined interval according to the information about the holder.

12. The tomography apparatus according to claim 2, wherein the slope filter, according to the information about the holder, absorbs radiation and forms the slope surface having a predetermined angle by combining the plurality of materials each having a slope surface.

13. The tomography apparatus according to claim 2, wherein the control unit controls the distribution of the transmitted radiation dose to a uniform distribution of radiation detected by the radiation detection unit.

* * * * *